United States Patent
Burkett et al.

[11] Patent Number: 5,918,590
[45] Date of Patent: Jul. 6, 1999

[54] HEAT CELLS

[75] Inventors: Timothy Alan Burkett, West Chester; Jody Marie Mesaros, Fairfield; Kenneth Stephen McGuire, Wyoming; Richard Keim White, Maineville, all of Ohio

[73] Assignee: The Procter & Gamble Company, Cincinnati, Ohio

[21] Appl. No.: 08/754,947

[22] Filed: Nov. 21, 1996

Related U.S. Application Data

[63] Continuation-in-part of application No. 08/604,694, Feb. 21, 1996, abandoned, which is a continuation-in-part of application No. 08/496,639, Jun. 29, 1995, abandoned.

[51] Int. Cl.⁶ ........................................................ F24J 1/00
[52] U.S. Cl. ...................... 126/263.02; 126/204; 607/114
[58] Field of Search .......................... 126/263.01, 263.02, 126/204; 607/114, 108–112

[56] References Cited

U.S. PATENT DOCUMENTS

| | | | |
|---|---|---|---|
| Re. 32,026 | 11/1985 | Yamashita et al. | 126/263 |
| 3,976,049 | 8/1976 | Yamashita et al. | 126/263 |
| 3,980,070 | 9/1976 | Krupa | 126/263 |
| 4,093,424 | 6/1978 | Yoshida et al. | 44/3 C |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,516,564 | 5/1985 | Koiso et al. | 126/263 |
| 4,649,895 | 3/1987 | Yasuki et al. | 126/263 |
| 4,756,299 | 7/1988 | Podella | 126/263 |
| 4,925,743 | 5/1990 | Ikeda et al. | 428/702 |
| 5,046,479 | 9/1991 | Usui | 126/204 |
| 5,233,981 | 8/1993 | Miyashita | 607/114 |
| 5,342,412 | 8/1994 | Ueki | 607/114 |
| 5,366,492 | 11/1994 | Ueki | 607/114 |

FOREIGN PATENT DOCUMENTS

| | | | |
|---|---|---|---|
| 1086110 | 5/1994 | China | A43B 7/02 |
| 0045642 | 2/1982 | European Pat. Off. . | |
| 160433 | 7/1987 | India | C09K 3/02 |
| 56-145846 | 11/1981 | Japan | A61F 7/03 |
| 56-170252 | 10/1982 | Japan | A61F 7/03 |
| 58-37075 | 3/1983 | Japan | C09K 5/00 |
| 58-132074 | 8/1983 | Japan | C09K 5/00 |
| 3-100090 | 4/1991 | Japan | C09K 5/00 |
| 4-2342 | 1/1992 | Japan | A61F 7/08 |
| 4-293989 | 10/1992 | Japan | C09K 5/00 |
| 5-81261 | 11/1993 | Japan | A61F 7/08 |
| 5-317188 | 12/1993 | Japan | A47J 36/28 |
| 6-1969 | 1/1994 | Japan | C09K 5/00 |
| 6-241575 | 8/1994 | Japan | F24J 1/02 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-124192 | 5/1995 | Japan | A61F 7/08 |
| 7-49042 | 5/1995 | Japan | A61F 7/08 |
| 7-194641 | 8/1995 | Japan | A61F 7/08 |
| 7-194642 | 8/1995 | Japan | A61F 7/08 |
| 8-126656 | 5/1996 | Japan | A61F 7/08 |
| 2205496 | 12/1988 | United Kingdom | A61F 7/03 |
| 2297490 | 8/1996 | United Kingdom | A61F 7/03 |
| 2 301 433 | 12/1996 | United Kingdom . | |

*Primary Examiner*—James C. Yeung
*Attorney, Agent, or Firm*—Loy M. White; Douglas C. Mohl; T. David Reed

[57] ABSTRACT

This invention relates to heat cells, based on a specific iron oxidation chemistry and having specific physical dimensions and fill characteristics. These heat cells, which can be incorporated into disposable body wraps, provide a controlled and sustained temperature for consistent, convenient, and comfortable heat application for treating temporary or chronic pain.

22 Claims, 2 Drawing Sheets

HEAT CELLS

CROSS REFERENCE TO RELATED APPLICATION

This application is a continuation-in-part of application Ser. No. 08/604,694, filed Feb. 21, 1996, now abandoned, which is a continuation-in-part of application Ser. No. 08/496,639, filed Jun. 29, 1995, now abandoned.

TECHNICAL FIELD

This invention relates to heat cells which contain a particulate exothermic composition.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like. These treatments include the use of whirlpools, hot towels, hydrocollators, heating pads and elastic compression bands. Many of these devices employ reusable thermal packs containing, e.g., water and microwaveable gels. In general, such devices which require the thermal source to be replenished are inconvenient to use. Further, many of these thermal units or devices do not provide long lasting heat and also do not maintain a consistent temperature over long periods of time. The skin temperature needs to be maintained from about 38° C. to about 41° C. but not above 45° C., as tissue damage occurs above 45° C., to achieve the desired therapeutic benefits.

The beneficial therapeutic effects from this administration of heat diminishes after the heat source is removed; therefore, it is desirable to provide a sustained heat source to the afflicted area for as long as possible, preferably for about eight hours. Disposable heat packs based on iron oxidation, such as those described in U.S. Pat. Nos. 4,366,804, 4,649, 895, 5,046,479 and Re. 32,026, are known and can provide long-lasting heat. However, such devices have proven not totally satisfactory because many of these devices cannot maintain a consistent and controlled temperature and/or such thermal devices are bulky and have unsatisfactory physical dimensions which hinder their effectiveness. Specifically, such devices cannot be easily incorporated into wraps which can comfortably conform to various body contours and hence deliver inconsistent, inconvenient and/or uncomfortable heat application to the body.

The present inventors have found that heat cells, based on a specific iron oxidation chemistry and having specific physical dimensions and fill characteristics, provide long lasting heat generation with improved temperature control. The heat cells of the present invention contain a particulate heat generating material which substantially fills the available cell volume within the cell reducing any excess void volume thereby minimizing the ability of the particulate matter to shift within the cell. This is accomplished without the need for any differential pressure across the cell wall. These heat cells, because of their adaptable physical dimensions, can be easily incorporated into disposable body wraps and the like which adapt to a wide variety of body contours, thus providing consistent, convenient, and comfortable heat application.

It is therefore an object of the present invention to provide heat cells which provide a controlled and sustained temperature and which reach their maximum temperature quickly. It is a further object of the present invention to provide heat cells which can be easily incorporated into disposable body wraps which adapt to a wide variety of body contours providing consistent, convenient and comfortable heat application.

These objectives and additional objectives will become readily apparent from the detailed description which follows.

SUMMARY OF THE INVENTION

A heat cell comprising:
  a particulate exothermic composition comprising:
    a.) from about 30% to about 80% iron powder;
    b.) from about 3% to about 25% activated carbon, non-activated carbon, and mixtures thereof;
    c.) from about 0.5% to about 10% metal salt; and
    d.) from about 1% to about 40% water;
  wherein the particles of said particulate exothermic composition are combined in a pocket, formed in a unified structure comprising at least two opposed surfaces, wherein at least one surface is oxygen permeable, that when filled with said particulate exothermic composition, has a fill volume and a cell volume whereby the ratio of fill volume to cell volume is from about 0.7 to about 1.0, wherein said ratio is maintained without the use of differential pressure across the cell wall, and further wherein the apex of said heat cell has a height of from greater than about 0.2 cm to about 1.0 cm.

All percentages and ratios used herein are by weight of the total composition, and all measurements made at 25° C., unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
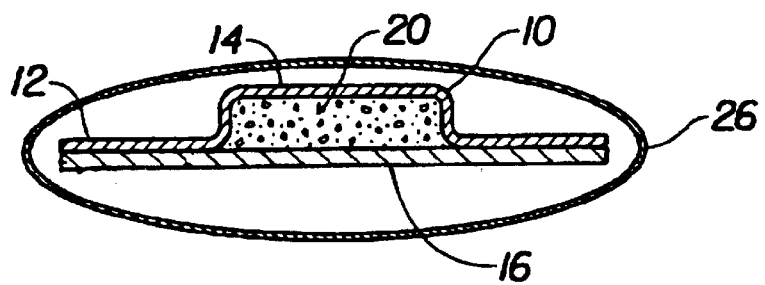
FIG. 1 is a sectional side view of a single heat cell, taken along section line 2—2 of FIG. 2, showing the particulate exothermic composition sealed between the first and second film layer substrates when the heat cell is protected from oxygen by being placed inside an impermeable pouch.
Figure 2:
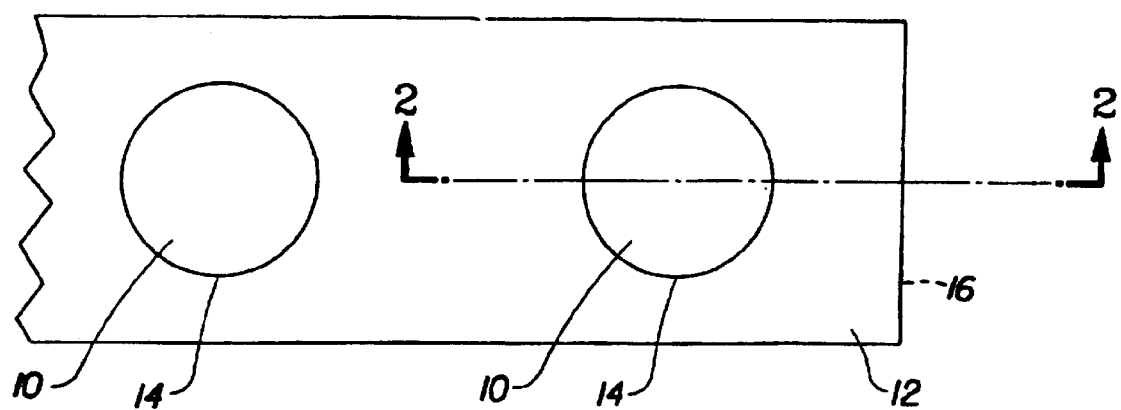
FIG. 2 is a top plan view of two heat cells connected together by continuous first and second film layer substrates.
Figure 3:
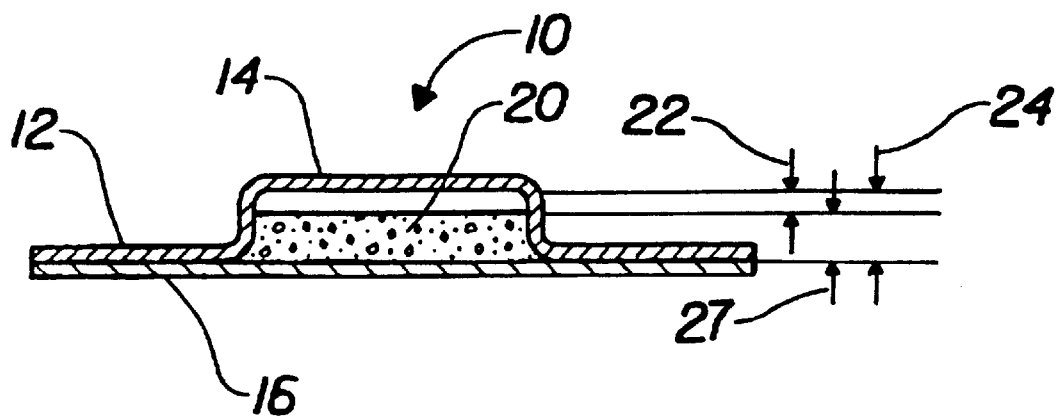
FIG. 3 is a sectional side view of a single heat cell, taken along section line 2—2 of FIG. 2, showing the key elements as well as the cell volume, fill volume, and void volume of the heat cell.

The particulate exothermic composition 20 comprises iron powder, carbon, a metal salt(s), and water.

Iron Powder

Iron is the anode for the electrochemical reaction involved in the exothermic oxidation of iron. Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air.

Typically, the iron powder comprises from about 30% to about 80% by weight, preferably from about 50% to about 70% by weight, of the particulate exothermic composition 20 of the present invention.

While oxygen is necessary for the oxidation reaction of iron to occur, an internal oxygen source is not required in the heat cells of the present invention, however, oxygen-producing chemical materials may be incorporated in the particulate exothermic composition 20 at the time of preparation thereof without changing the scope of the present invention. The oxygen sources used for the purpose of this invention include air and artificially made oxygen of various purity. Among these oxygen sources, air is preferred since it is the most convenient and inexpensive.

Activated and Non-activated Carbon

Activated carbon serves as the cathode for the electro-chemical reaction involved in the exothermic oxidation of iron. Active carbon is extremely porous in the inner structure giving it particularly good water-retention capabilities. Moreover, active carbon not only absorbs water well, but also adsorbs water vapor evaporated by the heat generation of the exothermic composition and helps prevent the escape of the water vapor. Therefore, it can also serve as a water-holding material. Further, active carbon can adsorb odors such as those caused by the oxidation of iron powder.

Active carbon prepared from coconut shell, wood, charcoal, coal, bone coal, etc. are useful, but those prepared from other raw materials such as animal products, natural gas, fats, oils and resins are also useful in the heat cells of the present invention. There is no limitation to the kinds of active carbon used, however, the preferred active carbon has superior water holding capabilities. The cathode capabilities can be extended by using non-activated carbon powder, i.e., carbon blended to reduce cost. Therefore, mixtures of the above carbons are useful in the present invention as well.

Typically, activated carbon, non-activated carbon, and mixtures thereof, comprises from about 3% to about 25%, preferably from about 8% to about 20%, most preferably from about 9% to about 15% by weight, of the exothermic compositions 20 of the present invention.

Metal Salts

The metal salt serves as a reaction promoter for activating the surface of the iron powder to ease the oxidation reaction with air and provides electrical conduction to the exothermic composition 20 to sustain the corrosive reaction. Useful metal salts include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used.

Among these metal salts, the deliquescent salts such as calcium chloride, magnesium chloride, etc. are very hygro-scopic and hence these compounds, even when added in a small amount, show an effectiveness in inhibiting the escape of water vapor. Sodium chloride shows small solubility difference vs. temperature difference and hence no crystal is precipitated at low temperatures, and also provides reasonable heat-generation. Thus, deviation of heat-generation due to temperature difference of atmospheric air does not occur. In general, several suitable alkali, alkaline earth, and transition metal salts exist which can also be used, alone or in combination, to sustain the corrosive reaction of iron.

The preferred metal salts of the present invention are sodium chloride, cupric chloride, and mixtures thereof Typically, the metal salt(s) comprises from about 0.5% to about 10% by weight, preferably from about 1.0% to about 5% by weight, of the particulate exothermic composition of the present invention.

Water

The water used herein may be from any appropriate source. There is no particular limitation to its purity, kind, etc. Typically, water comprises from about 1% to about 40% by weight, preferably from about 10% to about 30% by weight, of the particulate exothermic composition of the present invention.

Additional Components

In addition to the above described components of the particulate exothermic compositions 20 of the present invention, other components may also be added as appropriate.

Additional water-holding materials absorb the aqueous solution of reaction promoter, as does carbon, and serves the function of gradually supplying the promoter and water to the coexistent iron powder. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used.

Typically, the additional water-holding materials comprise from about 0.1% to about 30% by weight, preferably from about 5% to about 20% by weight, most preferably from about 1% to about 10% by weight, of the particulate exothermic composition 20 of the present invention.

Other additional components include oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoalu-minate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions 20 of the present invention, as appropriate, include extending agents such as metasilicates, zirconium, and ceramics.

Particle Size Range

Preferably at least 50%, more preferably 70%, even more preferably 80% and most preferably 90% of all of the particles by weight of the particulate exothermic composition 20 of the present invention have a mean particle size of less than 200 μm, preferably less than 150 μm.

Blending Ingredients

The above-mentioned components of the composition 20 are blended while being isolated from air using conventional blending techniques. Suitable methods of blending these components are described in detail in U.S. Pat. No. 4,649,895 to Yasuki et al., issued Mar. 17, 1987 which is incorporated by reference herein. For example, carbon is added to a blender or mixer, followed by a small amount of the total water and this combination is mixed. Usually enough water is added to assist in blending while avoiding escalated corrosion. Mixing is stopped and, in the absence of air, vermiculite is added to the carbon. Mixing is resumed until all the components are mixed thoroughly and iron powder is added and mixed. The composition is then blended until thoroughly mixed. Sodium chloride and the remaining water are mixed to form a brine solution which is then added to the particulate composition 20 during construction of the heat cell 10, as described below.

In the alternative, the above-mentioned components of the composition 20 can be blended while being isolated from air using conventional blending techniques. For example, carbon is added to a blender or mixer, followed by a small amount of the total water and this combination is mixed. Usually enough water is added to assist in blending while avoiding escalated corrosion. Mixing is stopped and, in the absence of air, vermiculite and sodium chloride are added to together. Mixing is resumed until all the components are mixed thoroughly and iron powder is added and mixed. The composition is then blended until thoroughly mixed. Additional water is added to the particulate composition during construction of the heat cell 10.

The particulate exothermic composition 20 is contained in the heat cells 10 as described below.

Heat Cell Construction

The heat cell 10 is formed in a unified structure comprising at least two opposed surfaces, preferably, film layer substrate surfaces 12 and 16, wherein at least one surface is oxygen permeable, that when filled with said particulate exothermic composition 20, has a fill volume 27, void volume 22, and a cell volume 24. The fill volume 27, as used herein, means the volume of the particulate composition in the filled heat cell 10. The void volume 22, as used herein, means the volume of the cell left unfilled by the particulate composition in a finished heat cell, measured without differential pressure in the heat cell 10 and without additional stretching or deformation of the substrate material. The cell volume 24, as used herein, means the fill volume plus the void volume of the heat cell. The ratio of fill volume 27 to cell volume 24 is from about 0.7 to about 1.0, preferably from about 0.75 to about 1.0, more preferably from about 0.8 to about 1.0, even more preferably from about 0.85 to about 1.0, and most preferably from about 0.9 to about 1.0 and wherein further the apex of said heat cell 10 has a height of from greater than about 0.2 cm to about 1.0 cm, preferably from greater than about 0.3 cm to about 0.9 cm, more preferably from about 0.4 cm to about 0.8 cm, and most preferably from about 0.5 cm to about 0.7 cm. The surfaces can be made of any suitable materials such as those described below.

The film layer substrates 12 and 16 of the present invention are preferably made of films or films laminated to nonwoven fabrics. In general the preferred films are those having heat sealability and capable of being easily thermally fused Nonwoven, if used, provide support and integretity to the film layer substrates. Examples of suitable films include polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber and synthetic rubber. The film layer substrates 12 and 16 thickness is in the range of about 1 to about 300 μm and may be oxygen permeable or impermeable. For the nonwoven fabrics, those having preferred characteristic properties of light weight and high tensile strength, e.g., nylon, rayon, cellulose ester, polyvinyl derivatives, polyolefins, polyamides, or polyesters, cuproammonium cellulose (Bemberg) and other high molecular weight compounds, as well as natural materials such as, wool, silk, jute, hemp, cotton, linen, sisal, or ramie, are suitable. These nonwoven materials are generally described in Riedel "Nonwoven Bonding Methods and Materials", *Nonwoven World,* (1987), incorporated herein by reference in its entirety. The preferred film layer substrates 12 and 16 of the present invention are polypropylene nonwoven sheets laminated to a film of poly(ethylene-vinyl acetate) or low-density polyethylene (LDPE) having a thickness of about 5 to about 100 μm.

The opposed surfaces 12 and 16 can be created by bonding two substrates together around their periphery thereby forming a pouch, envelope, or pocket 14 with the film side toward the inside of the pouch, envelope or pocket 14 (the side to be filled) and the nonwoven side to the outside. Pockets 14 can also be made in the substrates by thermoforming, mechanical embossing, vacuum embossing, or other acceptable means. Preferred for use herein is thermoforming which is described in "Thermoforming", *The Wiley Encyclopedia of Packaging Technology,* pp. 668–675 (1986), Marilyn Bakker, ed., incorporated herein by reference in its entirety.

The resulting heat cell 10 can have any geometric shape, e.g., disk, triangle, pyramid, cone, sphere, square, cube, rectangle, rectangular parallelepiped, cylinder, ellipsoid and the like. The preferred shape of the present invention comprises a disk shaped geometry having a cell diameter of from about 0.2 cm to about 5 cm, preferably from about 1 cm to about 4 cm, more preferably from about 2 cm to about 3 cm, and a height of from greater than about 0.2 cm to about 1 cm, preferably from greater than about 0.3 cm to about 0.9 cm, more preferably from about 0.4 cm to about 0.8 cm, and most preferably from about 0.5 cm to about 0.7 cm resulting in a cell volume of from about 0.0045 $cm^3$ to about 20 $cm^3$, preferably from about 0.2 $cm^3$ to about 11 $cm^3$. Alternatively, the shape of the present invention may also be elongated in its geometry, with the long axis parallel to the substrates, having a height of from about 0.2 cm to about 5 cm, preferably from greater than about 0.5 cm to about 1 cm, a width of from about 0.2 cm to about 20 cm, preferably from about 5 cm to about 10 cm, and a length of from about 1 cm to about 20 cm, preferably from about 5 cm to about 10 cm, resulting in a cell volume of from about 0.04 $cm^3$ to about 2000 $cm^3$, preferably from about 1.25 $cm^3$ to about 10 $cm^3$.

The heat cells 10 of the present invention preferably have a total surface area of below about 50 $cm^2$, preferably below about 40 $cm^2$, even more preferably below 25 $cm^2$, and more preferably below about 20 $cm^2$.

Heat cells 10 with this total surface area are easily incorporated into body wraps and the like which provide improved conformity with body forms.

Individual heat cells 10 can typically be prepared by adding a fixed amount of the particulate exothermic composition 20 to the pocket 14 in the polypropylene nonwoven/LDPE film layer substrate sheet 12. In this process, water or brine is added dropwise on top of the particulate exothermic composition 20, and a flat sheet of the polypropylene nonwoven/poly(ethylene-vinyl acetate) film layer substrate 16 is placed over the cell with the poly(ethylene-vinyl acetate) film side facing the LDPE film side of the preformed pocket containing sheet 12. The film layers of the two sheets 12 and 16 are bonded together using a low heat, forming a unified structure. The resulting heat cell 10 contains the particulate exothermic composition 20 sealed in the pocket 14 between the two film layer substrate sheets 12 and 16.

Alternatively, individual heat cells 10 can be prepared by using magnetic transfer of a fixed amount of the particulate exothermic composition 20 to the pocket 14 in the polypropylene nonwoven/LDPE film layer substrate sheet 12. That is, magnetic force is used to hold the particulate composition 20 in place on the film layer substrate surface 12. A second film layer substrate surface 16 is then placed over the first film layer substrate surface 12, such that the particulate composition 20 is between the two surfaces 12 and 16. The particulate composition 20 is then sealed between the first and second film layer substrate surfaces 12 and 16. Another alternative to the above described methods of preparing individual heat cells 10 uses vacuum to form a pocket 14. That is, vacuum is used to draw the film layer substrate surface 12 into a mold as the particulate composition 20 is placed on top of the film layer substrate surface 12 directly over the mold. The particulate composition 20 drops into the vacuum formed pocket 14 and is held in place by the vacuum and/or magnetic force exerted upon the particulate composition 20 in the bottom of the mold. A second film layer substrate surface 16 is then placed over the first film layer substrate surface 12, such that the particulate composition 20 is between the two surfaces 12 and 16. The particulate composition 20 is then sealed between the first and second film layer substrate surfaces 12 and 16.

Oxygen permeability can be provided by selecting films or film coatings for the film layer substrates 12 forming the pouches, envelopes, pockets 14, and/or covering layer 16, that have the specifically desired permeability properties. The desired permeability properties may be provided by microporous films or by films which have pores or holes formed therein. The formation of these holes/pores may be via extrusion cast/vacuum formation or by hot needle aperturing. Oxygen permeability can also be provided in the present invention by perforating at least one of the film layer substrates with aeration holes using, for example, at least one pin, preferably an array of from about 20 to about 60 pins, with, e.g., tapered points and diameters of from about 0.2 mm to about 2 mm, preferably from about 0.4 mm to about 0.9 mm.

Alternatively, after the film layer substrates 12 and 16 have been bonded together, enclosing the particulate composition 20 in the pocket 14 between them, one side of the heat cell 10 may be perforated with aeration holes using, for example, at least one pin, preferably an array of from about 20 to about 60 pins, with, e.g., tapered points and diameters of from about 0.2 mm to about 2 mm, preferably from about 0.4 mm to about 0.9 mm. The pins are pressed through one side of the heat cell material to a depth of from about 2% to about 100%, preferably from about 20% to about 100%, and more preferably from about 50% to about 100% into the particulate exothermic composition. This hole configuration provides an oxygen diffusion into the heat cell during oxidation of the particulate exothermic composition of from about 0.01 cc $O_2$/min./5 cm$^2$ to about 15.0 cc $O_2$/min./5 cm$^2$ (at 21° C., 1 ATM), preferably from about 0.9 cc $O_2$/min./5 cm$^2$ to about 3 cc $O_2$/min./5 cm$^2$ (at 21° C., 1 ATM). Although there is preferably provided aeration holes in the upper covering film layer 16, it is also possible to provide aeration holes in the lower covering film layer 12, and/or both 12 and 16.

The velocity, duration, and temperature of the thermogenic oxidation reaction of the particulate exothermic composition 20 can be controlled as desired by changing the area of contact with air, more specifically, by changing the oxygen diffusion/permeability.

The heat cells 10 of the present invention may optionally incorporate a component, such as a separate substrate layer or incorporated into at least one of the film layer substrates, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof. The heat cells 10 may also comprise a separate substrate layer, or incorporated into at least one of the film layer substrates, a self-adhesive component and/or a sweat-absorbing component.

Second Packaging

These heat cells 10 can be used alone, or can be incorporated into various wraps. Typically, these wraps have a means for retaining the wraps in place around various parts of the body, such as knee, neck, back, etc. and can comprise any number of styles and shapes.

The finished heat cell 10 is packaged in a secondary air-impermeable package 26 to prevent the oxidation reaction from occurring until desired as described in the aforementioned U.S. Pat. No. 4,649,895, already incorporated herein by reference. Alternatively, air impermeable removable adhesive strips can be placed over the aeration holes in the heat cells 10 such that, when the strips are removed, air is allowed to enter the heat cell 10, thus activating the oxidation reaction of the iron powder.

EXAMPLES

The following examples further describe and demonstrate preferred embodiments within the scope of the present invention. The examples are given solely for the purpose of illustration, and are not to be construed as limitations of the present invention, as many variations thereof are possible without departing from its spirit and scope of the invention.

Example 1

A heat cell is prepared as follows. The following components are combined using conventional blending techniques to form a particulate composition.

Thirty-six grams of carbon and 25 grams of water are placed into a blender or mixer and mixed until all the water is absorbed by the carbon. Six grams of vermiculite are added to the carbon and the composition is thoroughly mixed. One hundred seventy-two grams of iron are then added to the composition and the mix is again mixed thoroughly.

Approximately 2.4 grams of the above particulate exothermic composition are added to a preformed pocket, which has been thermoformed to form the pocket, in a sheet of polypropylene nonwoven that has been coated with a film of LDPE. Ten grams of sodium chloride are mixed with 61 grams of water to form a 14.3% brine solution, which is then added dropwise (approximately 0.7 grams per cell) to the ingredients described above. The final exothermic particulate composition comprises:

| Ingredients | W/W % |
| --- | --- |
| Iron | 55.2 |
| Activated Carbon | 11.7 |
| Sodium Chloride | 3.3 |
| Vermiculite | 2.0 |
| Water | 27.8 |

Twenty-six pins, of approximately 0.5 mm diameter are pressed simultaneously into a flat polypropylene nonwoven sheet coated with poly(ethylene-vinyl acetate). This perforation process results in a diffusive $O_2$ permeability of about 2 cc/min./5 cm$^2$ (at 21° C., 1 ATM). The flat polypropylene nonwoven sheet coated with poly(ethylene-vinyl acetate) is then placed over the heat cell, such that the perforations are located over the exothermic particulate composition, and heat bonded to the bottom sheet. The cell height is 0.64 cm and the diameter is 2.5 cm. The resulting fill volume to cell volume ratio is approximately 0.89. Material around the heat cell is trimmed to provide 2.5 cm of excess material around the perimeter of the cell. The cell begins to generate heat shortly after the brine is added to the particulate composition, therefore the top and bottom sheets are bonded and the finished heat cell is quickly packaged in an air tight secondary packaging for future use.

This cell can also be incorporated into, for example, body wraps.

Example 2

A heat cell is prepared as follows. The following components are combined using conventional blending techniques to form a particulate composition.

| Ingredients | W/W % |
| --- | --- |
| Iron | 74.0 |
| Activated Carbon | 15.5 |
| Cupric Chloride | 3.5 |
| Vermiculite | 2.5 |
| Calcium hydroxide | 1.0 |

These components are blended with 3.5% water by weight of this particulate composition.

Approximately 8 grams of the above particulate exothermic composition are added to the disk shaped preformed pocket, which has been thermoformed to form the pocket, in a sheet of polypropylene nonwoven that has been coated with a film of LDPE. The cell height is 0.48 cm and the diameter is 5 cm. The resulting fill volume to cell volume ratio is approximately 0.83. Additional water is added dropwise to the ingredients described above to produce the final exothermic particulate composition.

A flat polypropylene nonwoven sheet coated with poly(ethylene-vinyl acetate) is then placed over the heat cell and heat bonded to the bottom sheet. Material around the heat cell is trimmed to provide 2.5 cm of excess material around the perimeter of the cell. One hundred pins of approximately 0.5 mm diameter are pressed simultaneously into one side of the cell until they penetrate approximately 100% into the exothermic composition, but not through the bottom sheet. This perforation process results in a diffusive $O_2$ permeability of about 1 cc/min./5 cm$^2$ (at 21° C., 1 ATM). The cell begins to generate heat shortly after pin penetration.

This cell can also be incorporated into, for example, body wraps and/or packaged in air tight secondary packaging for future use.

Example 3

Approximately 4 grams of the particulate exothermic composition prepared according to Example 1 are added to the disk shaped preformed pocket, which has been thermoformed to form the pocket, in a sheet of polypropylene nonwoven that has been coated with a film of LDPE. The cell height is 0.95 cm and the diameter is 2.5 cm. The resulting fill volume to cell volume ratio is approximately 0.75. A brine solution is then added dropwise to the ingredients as described in Example 1, to produce the final exothermic particulate composition. A flat polypropylene nonwoven sheet coated with poly(ethylene-vinyl acetate) is then placed over the heat cell and bonded to the bottom sheet. Material around the heat cell is trimmed to provide 2.5 cm of excess material around the perimeter of the cell. Twenty-six pins of approximately 0.5 mm diameter are pressed simultaneously into one side of the cell until they penetrate approximately 80% into the exothermic composition. This perforation process results in a diffusive $O_2$ permeability of about 1 cc/min./5 cm$^2$ (at 21° C., 1 ATM). The cell begins to generate heat shortly after pin penetration.

This cell can also be incorporated into, for example, body wraps and/or packaged in air tight secondary packaging for future use.

Example 4

Approximately 2.8 grams of the particulate exothermic composition prepared according to Example 1 are added to the disk shaped preformed pocket, which has been thermoformed to form the pocket, in a sheet of polypropylene nonwoven that has been coated with a film of LDPE. The cell height is 0.64 cm and the diameter is 2.5 cm. The resulting fill volume to cell volume ratio is approximately 0.89. A brine solution is then added dropwise to the ingredients as described in Example 1 to produce the final exothermic particulate composition. A flat polypropylene nonwoven sheet coated with poly(ethylene-vinyl acetate) is then placed over the heat cell and bonded to the bottom sheet. Material around the heat cell is trimmed to provide 2.5 cm of excess material around the perimeter of the cell. Eight pins of approximately 1.5 mm diameter are pressed simultaneously into one side of the cell until they penetrate approximately 20% into the exothermic composition. This perforation process results in a diffusive $O_2$ permeability of about 1 cc/min./5 cm$^2$ (at 21° C., 1 ATM). The cell begins to generate heat shortly after pin penetration.

This cell can also be incorporated into, for example, body wraps and/or packaged in air tight secondary packaging for future use.

Example 5

Approximately 2 grams of the particulate exothermic composition described in Example 1 are added to the disk shaped preformed pocket, which has been thermoformed to form the pocket, in a sheet of polypropylene nonwoven that has been coated with a film of LDPE. The cell height is 0.47 cm and the diameter is 2.5 cm. The resulting fill volume to cell volume ratio is approximately 0.83. A brine solution is then added dropwise to the ingredients as described in Example 1 to produce the final exothermic particulate composition. A flat polypropylene nonwoven sheet coated with poly(ethylene-vinyl acetate) is then placed over the heat cell and bonded to the bottom sheet. Material around the heat cell is trimmed to provide 1.0 cm of excess material around the perimeter of the cell. Twenty-six pins of approximately 0.5 mm diameter are pressed simultaneously into one side of the cell until they penetrate approximately 100% into the exothermic composition, but not through the bottom sheet. This perforation process results in a diffusive $O_2$ permeability of about 1 cc/min./5 cm$^2$ (at 21° C., 1 ATM). The cell begins to generate heat shortly after pin penetration.

This cell can also be incorporated into, for example, body wraps and/or packaged in air tight secondary packaging for future use.

Example 6

Approximately 14 grams of the particulate exothermic composition prepared according to Example 1 are added to the rectangular shaped preformed pocket, which has been thermoformed to form the pocket, in a sheet of polypropylene nonwoven that has been coated with a film of LDPE. The cell height is 0.5 cm and the width is 5 cm and the length is 6.5 cm. The resulting fill volume to cell volume ratio is approximately 0.85. A brine solution is then added dropwise to the ingredients as described in Example 1, to produce the final exothermic particulate composition. A flat polypropylene nonwoven sheet coated with poly(ethylene-vinyl acetate) is then placed over the heat cell and bonded to the bottom sheet. Material around the heat cell is trimmed to provide 2.5 cm of excess material around the perimeter of the cell. Twenty-six pins of approximately 0.5 mm diameter are pressed simultaneously into one side of the cell until they penetrate approximately 80% into the exothermic composition. This perforation process results in a diffusive $O_2$ permeability of about 2 cc/min./5 cm$^2$ (at 21° C., 1 ATM). The cell begins to generate heat shortly after pin penetration.

This cell can also be incorporated into, for example, body wraps and/or packaged in air tight secondary packaging for future use.

What is claimed is:

1. A heat cell comprising:
    a particulate exothermic composition comprising:
        a.) from about 30% to about 80% by weight, iron powder;
        b.) from about 3% to about 25% by weight, activated carbon, non-activated carbon, and mixtures thereof;
        c.) from about 0.5% to about 10% by weight metal salt; and
        d.) from about 1% to about 40% by weight, water;
    wherein the particles of said particulate exothermic composition are combined in a pocket, formed in a unified structure comprising at least two opposed surfaces, wherein at least one surface is oxygen permeable, that when filled with said particulate exothermic composition, has a fill volume and a cell volume whereby the ratio of fill volume to cell volume is from about 0.7 to about 1.0, wherein said ratio is maintained without the use of differential pressure across the cell wall, and further wherein the apex of said heat cell has a height of from greater than about 0.2 cm to about 1.0 cm.

2. A heat cell according to claim 1 further comprising from about 0.1% to about 30% by weight, of additional water-holding material.

3. A heat cell according to claim 1 wherein at least 80% of the particles of said particulate exothermic composition have a mean particle size of less than 200 μm.

4. A heat cell according to claim 3 wherein said heat cell has a total surface area of less than about 40 cm$^2$.

5. A heat cell according to claim 1 wherein at least 90% of the particles of said particulate exothermic composition have a mean particle size of less than 150 μm.

6. A heat cell according to claim 5 wherein said heat cell has a total surface area of less than about 20 cm$^2$.

7. A heat cell according to claim 6 wherein said heat cell has a height of from greater than about 0.3 cm to about 0.9 cm.

8. A heat cell according to claim 7 wherein said heat cell is in a shape selected from the group consisting of a disk, triangle, pyramid, cone, sphere, square, cube, rectangle, rectangular parallelepiped, cylinder, and ellipsoid.

9. A heat cell according to claim 8 in the shape of a disk having a diameter of from about 2 cm to about 3 cm and a height of from about 0.4 cm to about 0.8 cm.

10. A heat cell according to claim 9 wherein said metal salt is selected from the group consisting of alkali metal salts, alkaline earth metal salts, and mixtures thereof.

11. A heat cell according to claim 10 wherein said metal salt is sodium chloride, cupric chloride, and mixtures thereof.

12. A heat cell according to claim 11 wherein said additional water holding material is vermiculite.

13. A heat cell according to claim 12 further wherein said heat cell is formed from a film coated, air-impermeable substrate comprising at least one aeration hole having a diameter of from about 0.2 mm to about 2 mm penetrating at least one of the external surfaces of said pocket.

14. A heat cell according to claim 13 wherein said heat cell is formed from a film coated, air-impermeable substrate comprising from about 20 to about 60 aeration holes having a diameter of from about 0.4 mm to about 0.9 mm penetrating at least one of the external surfaces of said pocket.

15. A heat cell comprising:
    a particulate exothermic composition comprising:
        a.) from about 30% to about 80% by weight, iron powder;
        b.) from about 3% to about 25% by weight, activated carbon, non-activated carbon, and mixtures thereof;
        c.) from about 0.5% to about 10% by weight, metal salt; and
        d.) from about 1% to about 40% by weight, water;
    wherein the particles of said particulate exothermic composition are combined in a pocket, having an elongated shape, with the long axis parallel to the film layer substrates of the unified structure comprising at least two opposed surfaces, wherein at least one surface is oxygen permeable, that when filled with said particulate exothermic composition, has a fill volume and a cell volume whereby the ratio of fill volume to cell volume is from about 0.7 to about 1.0, wherein said ratio is maintained without the use of differential pressure across the cell wall, and further wherein the width of said heat cell at its widest point is from about 0.2 cm to about 20 cm, the height at its apex of from about 0.2 cm to about 5 cm, and the length is from about 1 cm to about 20 cm.

16. A heat cell according to claim 15 further comprising from about 0.1% to about 30% by weight, of additional water-holding material.

17. A heat cell according to claim 15 wherein at least 80% of the particles of said particulate exothermic composition have a mean particle size of less than 200 μm.

18. A heat cell according to claim 17 comprising a width at its widest point of from about 2 cm to about 3 cm, a height of from greater than about 0.5 cm to about 1.0 cm, and a length of from about 5 cm to about 10 cm.

19. A heat cell according to claim 17 wherein said metal salt is selected from the group consisting of alkali metal salts, alkaline earth metal salts, and mixtures thereof.

20. A heat cell according to claim 19 wherein said metal salt is sodium chloride, cupric chloride, and mixtures thereof.

21. A heat cell according to claim 20 wherein said water holding material is vermiculite.

22. A heat cell according to claim 21 further wherein said heat cell is formed from a film coated air-impermeable substrate comprising at least one aeration hole having a diameter of from about 0.2 mm to about 2 mm penetrating at least one of the external surfaces of said pocket.

* * * * *